United States Patent [19]

Nakagawa et al.

[11] Patent Number: 5,449,672
[45] Date of Patent: Sep. 12, 1995

[54] ALKYLAMINOALKYLPYRROLIDINYLTHIOCARBAPENEM DERIVATIVES

[75] Inventors: Susumu Nakagawa; Shinji Kato; Satoshi Murase; Osamu Okamoto; Ryuji Mitomo; Katsumi Yamamoto; Koji Yamada; Hiroshi Fukatsu, all of Tsukuba, Japan

[73] Assignee: Banyu Pharmaceutical Co., Ltd., Tokyo, Japan

[21] Appl. No.: 289,547

[22] Filed: Aug. 12, 1994

Related U.S. Application Data

[63] Continuation of Ser. No. 982,511, Nov. 27, 1992, abandoned.

[30] Foreign Application Priority Data

Nov. 27, 1991 [JP] Japan ............................ 3-335889

[51] Int. Cl.$^6$ .................... C07D 487/04; A61K 31/40
[52] U.S. Cl. ........................ 514/210; 540/350
[58] Field of Search ............ 540/350, 310; 514/210

[56] References Cited

U.S. PATENT DOCUMENTS

| | | | |
|---|---|---|---|
| 4,962,103 | 10/1990 | Sunagawa et al. | 514/210 |
| 5,093,328 | 3/1992 | Sunagawa et al. | 540/350 |
| 5,100,888 | 3/1992 | Nakagawa et al. | 540/350 |

FOREIGN PATENT DOCUMENTS

| | | |
|---|---|---|
| 0182213 | 5/1986 | European Pat. Off. . |
| 0243686 | 11/1987 | European Pat. Off. . |
| 0435320 | 7/1991 | European Pat. Off. . |

*Primary Examiner*—Nicholas Rizzo
*Attorney, Agent, or Firm*—Oblon, Spivak, McClelland, Maier & Neustadt

[57] ABSTRACT

A compound of the formula:

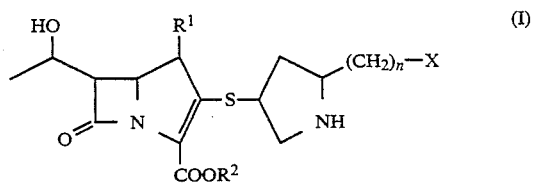

wherein $R^1$ is a hydrogen atom or a methyl group, $R^2$ is a hydrogen atom or a negative charge, X is a group of $-N(R^3)R^4$ (wherein $R^3$ is a lower alkyl group, and $R^4$ is a hydrogen atom or a lower alkyl group) or a group of $-N^+(R^5)(R^6)R^7$ (wherein each of $R^5$, $R^6$ and $R^7$ which may be the same or different, is a lower alkyl group), and n is an integer of from 2 to 4; or a pharmaceutically acceptable salt or ester thereof.

5 Claims, No Drawings

ALKYLAMINOALKYLPYRROLIDINYLTHIOCARBAPENEM DERIVATIVES

This application is a continuation of application Ser. No. 07/982,511, filed on Nov. 27, 1992 now abandoned.

The present invention relates to novel carbapenem (7-oxo-1-azabicyclo[3.2.0]hept-2-en-2-carboxylic acid) compounds, antibacterial agents containing such compounds as active ingredients, and a process for producing such compounds.

In recent years, new β-lactam antibiotic substances have been found in nature which have the same β-lactam rings as penicillin derivatives and as cephalosporin derivatives, but which have different basic structures.

For example, naturally derived carbapenem compounds such as thienamycin isolated from the fermentation of Streptomyces cattleya (J. Am. Chem. Soc., vol. 100, p.6491 (1978)), may be mentioned. Thienamycin has an excellent antibacterial spectrum and strong antibacterial activities over a wide range against gram positive bacteria and gram negative bacteria. Therefore, its development as a highly useful β-lactam agent has been expected. However, thienamycin itself is chemically unstable, and it has been reported that it is likely to be decomposed by a certain enzyme in vivo such as renal dehydropeptidase I (hereinafter referred to simply as DHP-I), whereby the antibacterial activities tend to decrease, and the recovery rate in the urine is low (Antimicrob. Agents Chemother., vol. 22, p.62 (1982); ditto, vol. 23, p.300 (1983)).

Merck & Co., Inc. have synthesized many thienamycin analogues with an aim to maintain the excellent antibacterial activities of thienamycin and to secure chemical stability. As a result, imipenem, (5R,6S,8R)-3-[[2-(formimidoylamino)ethyl]thio]-6-(1-hydroxyethyl)-7-oxo-1-azabicyclo[3.2.0]hept-2-en-2-carboxylic acid monohydrate, obtained by formimidation of the amino group of thienamycin, has been practically developed as a pharmaceutical product (J. Med. Chem., vol. 22, p. 1435 (1979)). Imipenem has antibacterial activities of an equal or higher level than thienamycin against various types of bacteria and has β-lactamase resistance. Especially against Pseudomonas aeruginosa, its antibacterial activities are superior to thienamycin by from 2 to 4 times. Further, the stability of imipenem in the solid form or in an aqueous solution is remarkably improved over thienamycin.

However, like thienamycin, imipenem is likely to be decomposed by DHP-I in the human kidney. Therefore, it can not be used for treatment of the urinary-tract infection. Further, it presents toxicity against the kidney due to the decomposition products. Therefore, imipenem can not be administered alone and is required to be used in combination with a DHP-I inhibitor like cilastatin (J. Antimicrob. Chemother., vol. 12 (Suppl. D), p. 1 (1983)). In recent years, imipenem has been frequently used for the treatment and prevention of infectious diseases. Consequently, highly methicillin resistant Staphylococcus aureus which is resistant to imipenem and imipenem resistant Pseudomonas aeruginosa are increasing in the clinical field. Imipenem does not show adequate treating effects against these resistant bacteria.

As the prior art closest to the present invention, European Patent Publication No. 182213 may be mentioned. This publication generally describes in its claims carbapenem compounds including those wherein the side chain at the 2-position of the carbapenem structure is a 2-(substituted)pyrrolidin-4-ylthio group, and the substituent is an amino-$C_{1-6}$ alkyl group which may be protected. However, among these carbapenem compounds, the one having an aminoalkyl group at the 2-position of the pyrrolidinyl group is limited to a compound having an (acetylamino)methyl group [the compound of specific example 24 in European Patent Publication No. 182213 (p. 116) (the compound of REFERENCE EXAMPLE 3 in this specification) or the compound of specific example 23 (EXAMPLE 19)], i.e. a compound wherein the amino group is protected by an acetyl group. Therefore, carbapenem compounds having, as a feature of the present invention, an amino group substituted by at least one lower alkyl group (a secondary or tertiary amino group or an ammonio group) at the terminal of the $C_{2-4}$ alkylene group of the side chain at the 2-position of the pyrrolidinyl group substituted at the 2-position of the carbapenem structure, are not disclosed in the publication, and they are novel compounds not disclosed or suggested in any other prior art literatures or patent specifications.

β-Lactam antibiotics exhibit selective toxicity against bacteria and show no substantial effects against animal cells. Therefore, they are widely used for treatment of infectious diseases caused by bacteria, as rare antibiotics having little side effects, and thus are highly useful drugs.

However, in recent years, highly methicillin resistant Staphylococcus aureus and resistant Pseudomonas aeruginosa have been isolated frequently from patients with the immunity decreased, as bacteria causing hardly curable infectious diseases. This is regarded as a clinically serious problem. Accordingly, it is strongly desired to develop an antibacterial agent having improved antibacterial activities against such resistant bacteria. Especially with respect to carbapenem compounds, it is desired to improve the antibacterial activities, to improve the stability against DHP-I, to reduce the toxicity against the kidney and to reduce side effects against the central nervous system.

The compounds disclosed in the above-mentioned European Patent Publication No. 182213 show good antibacterial activities, but their antibacterial activities particularly against the above-mentioned highly methicillin resistant Staphylococcus aureus and resistant Pseudomonas aeruginosa are not adequate. Accordingly, a carbapenem compound having superior antibacterial activities, is still desired.

The present inventors have made extensive researches with an aim to provide novel carbapenem compounds which have excellent antibacterial activities and which are resistant against DHP-I. As a result, they have found that carbapenem compounds of the present invention having, at the 2-position of the carbapenem structure, a group of the formula:

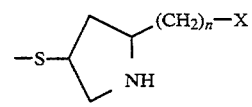

wherein X is a group of $-N(R^3)R^4$ (wherein $R^3$ is a lower alkyl group, and $R^4$ is a hydrogen atom or a lower alkyl group) or a group of $-N^+(R^5)(R^6)R^7$ (wherein each of $R^5$, $R^6$ and $R^7$ which may be the same or different, is a lower alkyl group), and n is an integer of from 2 to 4, are novel compounds not disclosed in any literatures, and that such compounds have strong antibacterial activities against gram positive bacteria such as *Staphylococcus aureus* and against gram negative bacteria including *Pseudomonas aeruginosa* and further exhibit excellent stability against DHP-I. The present invention has been accomplished on the basis of this discovery.

The present invention provides a compound of the formula:

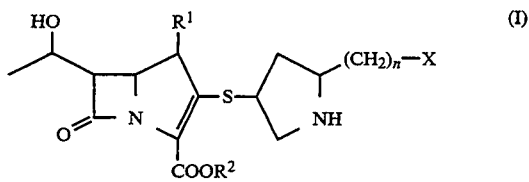

wherein $R^1$ is a hydrogen atom or a methyl group, $R^2$ is a hydrogen atom or a negative charge, X is a group of $-N(R^3)R^4$ (wherein $R^3$ is a lower alkyl group, and $R^4$ is a hydrogen atom or a lower alkyl group) or a group of $-N^+(R^5)(R^6)R^7$ (wherein each of $R^5$, $R^6$ and $R^7$ which may be the same or different, is a lower alkyl group), and n is an integer of from 2 to 4; or a pharmaceutically acceptable salt or ester thereof.

The present invention also provides a process for producing the compound of the formula (I) or a pharmaceutically acceptable salt or ester thereof, which comprises reacting a compound of the formula:

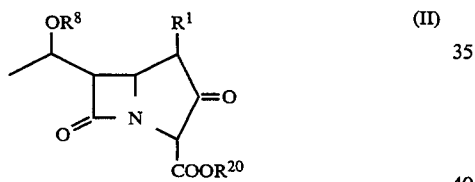

wherein $R^1$ is as defined above, $R^8$ is a hydrogen atom or a hydroxyl-protecting group, and $R^{20}$ is a hydrogen atom or a carboxyl-protecting group, or a reactive derivative thereof, with a compound of the formula:

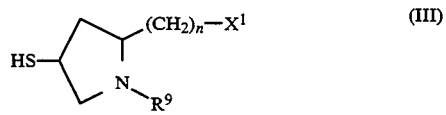

wherein $R^9$ is a hydrogen atom or an imino-protecting group, $X^1$ is a group of $-N(R^3)R^{40}$ (wherein $R^3$ is as defined above, and $R^{40}$ is a hydrogen atom, a lower alkyl group or an imino-protecting group) or a group of $-N^+(R^5)(R^6)R^7$ (wherein $R^5$, $R^6$ and $R^7$ are as defined above), and n is as defined above, to obtain a compound of the formula:

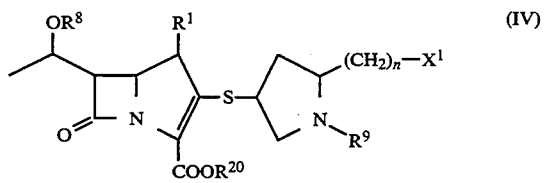

wherein $R^1$, $R^8$, $R^9$, $R^{20}$, $X^1$ and n are as defined above, and if necessary, removing any protecting group of the compound of the formula (IV).

Further, the present invention provides an antibacterial agent comprising an antibacterially effective amount of the compound of the formula (I) or a pharmaceutically acceptable salt or ester thereof, and a pharmaceutically acceptable carrier or diluent.

The compounds of the present invention are novel compounds not disclosed in literatures and have strong antibacterial activities against sensitive or resistant gram positive bacteria and gram negative bacteria and excellent stability against β-lactamase and DHP-I, and they are thus useful as antibacterial agents.

Now, the present invention will be described in detail with reference to the preferred embodiments. Firstly, the symbols and terms used in this specification will be explained.

The compound of the present invention has a basic structure of the formula:

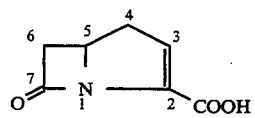

which is systematically referred to as a 7-oxo-1-azabicyclo[3.2.0]hept-2-en-2-carboxylic acid. For the convenience sake, in this specification, this basic structure will be referred to as a 1-carbapen-2-em-3-carboxylic acid by putting the numbers based on a commonly widely used carbapenem of the formula:

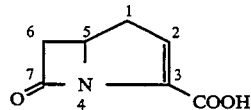

The present invention includes optical isomers based on the asymmetrical carbon atoms at the 1-position, 5-position, 6-position and 8-position of the carbapenem structure and stereoisomers. Among these isomers, preferred is a compound of a (5R,6S,8R) configuration i.e. a compound having a steric configuration of (5R,6S) (5,6-trans) like thienamycin and in which the carbon atom at the 8-position takes a R-configuration, or a compound of a (1R,5S,6S,8R) configuration in a case where a methyl group is present at the 1-position.

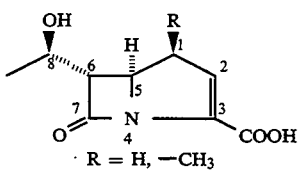

R = H, $-CH_3$

Also with respect to the 2-substituted pyrrolidin-4-ylthio group of the side chain at the 2-position, the present invention includes isomers based on the asymmetrical carbon atoms at the 2-position and 4-position of the pyrrolidine structure and in the side chain at the 2-position. Among these isomers, preferred are compounds having a (2'R,4'S) configuration or a (2'S,4'R) configuration.

Further, with respect to the side chain substituted at the 2-position of the pyrrolidine structure, there exist isomers based on asymmetrical carbons, and the present invention includes such isomers as well.

The lower alkyl group means a linear or branched alkyl group having from 1 to 6 carbon atoms, such as a methyl group, an ethyl group, a propyl group, an isopropyl group, a butyl group, a sec-butyl group, a tert-butyl group, a pentyl group or a hexyl group, preferably a methyl group, an ethyl group or a tert-butyl group.

The carboxyl-protecting group may, for example, be a lower alkyl group such as a methyl group, an ethyl group, a propyl group, an isopropyl group or a tert-butyl group; a halogenated lower alkyl group such as a 2,2,2-trichloroethyl group or a 2,2,2-trifluoroethyl group; a lower alkanoyloxyalkyl group such as an acetoxymethyl group, a propionyloxymethyl group, a pivaloyloxymethyl group, a 1-acetoxyethyl group or a 1-propionyloxyethyl group; a lower alkoxycarbonyloxyalkyl group such as a 1-(methoxycarbonyloxy)ethyl group, a 1-(ethoxycarbonyloxy)ethyl group or a 1-(isopropoxycarbonyloxy)ethyl group; a lower alkenyl group such as a 2-propenyl group, a 2-chloro-2-propenyl group, a 3-methoxycarbonyl-2-propenyl group, a 2-methyl-2-propenyl group, a 2-butenyl group or a cinnamyl group; an aralkyl group such as a benzyl group, a p-methoxybenzyl group, a 3,4-dimethoxybenzyl group, an o-nitrobenzyl group, a p-nitrobenzyl group, a benzhydryl group or a bis(p-methoxyphenyl)methyl group; a (5-substituted 2-oxo-1,3-dioxol-4-yl)methyl group such as a (5-methyl-2-oxo-1,3-dioxol-4-yl)methyl group; a lower alkylsilyl group such as a trimethylsilyl group or a tert-butyldimethylsilyl group; an indanyl group, a phthalidyl group or a methoxymethyl group. Particularly preferred are a 2-propenyl group, a p-nitrobenzyl group, a p-methoxybenzyl group, a benzhydryl group and a tert-butyldimethylsilyl group.

The hydroxyl-protecting group may, for example, be a lower alkylsilyl group such as a trimethylsilyl group or a tert-butyldimethylsilyl group; a lower alkoxymethyl group such as a methoxymethyl group or a 2-methoxyethoxymethyl group; a tetrahydropyranyl group; an aralkyl group such as a benzyl group, a p-methoxybenzyl group, a 2,4-dimethoxybenzyl group, an o-nitrobenzyl group, a p-nitrobenzyl group or a trityl group; an acyl group such as a formyl group or an acetyl group; a lower alkoxycarbonyl group such as a tert-butoxycarbonyl group, a 2-iodoethoxycarbonyl group or a 2,2,2-trichloroethoxycarbonyl group; an alkenyloxycarbonyl group such as a 2-propenyloxycarbonyl group, a 2-chloro-2-propenyloxycarbonyl group, a 3-methoxycarbonyl-2-propenyloxycarbonyl group, a 2-methyl-2-propenyloxycarbonyl group, a 2-butenyloxycarbonyl group or a cinnamyloxycarbonyl group; or an aralkyloxycarbonyl group such as a benzyloxycarbonyl group, a p-methoxybenzyloxycarbonyl group, an o-nitrobenzyloxycarbonyl group or a p-nitrobenzyloxycarbonyl group. Particularly preferred are a 2-propenyloxycarbonyl group, a p-nitrobenzyloxycarbonyl group and a tert-butyldimethylsilyl group.

The imino-protecting group may, for example, be an aralkylidene group such as a benzylidene group, a p-chlorobenzylidene group, a p-nitrobenzylidene group, a salicylidene group, an α-naphthylidene group or a β-naphthylidene group; an aralkyl group such as a benzyl group, a p-methoxybenzyl group, a 3,4-dimethoxybenzyl group, an o-nitrobenzyl group, a p-nitrobenzyl group, a benzhydryl group, a bis(p-methoxyphenyl)methyl group or a trityl group; a lower alkanoyl group such as a formyl group, an acetyl group, a propionyl group, a butyryl group, an oxalyl group, a succinyl group, or a pivaloyl group; a halogenated lower alkanoyl group such as a chloroacetyl group, a dichloroacetyl group, a trichloroacetyl group or a trifluoroacetyl group; an arylalkanoyl group such as a phenylacetyl group or a phenoxyacetyl group; a lower alkoxycarbonyl group such as a methoxycarbonyl group, an ethoxycarbonyl group, a propoxycarbonyl group or a tert-butoxycarbonyl group; a halogenated lower alkoxycarbonyl group such as a 2-iodoethoxycarbonyl group or a 2,2,2-trichloroethoxycarbonyl group; an alkenyloxycarbonyl group such as a 2-propenyloxycarbonyl group, a 2-chloro-2-propenyloxycarbonyl group, a 3-methoxycarbonyl-2-propenyloxycarbonyl group, a 2-methyl-2-propenyloxycarbonyl group, a 2-butenyloxycarbonyl group or a cinnamyloxycarbonyl group; an aralkyloxycarbonyl group such as a benzyloxycarbonyl group, an o-nitrobenzyloxycarbonyl group, a p-nitrobenzyloxycarbonyl group or a phenethyloxycarbonyl group; or a lower alkylsilyl group such as a trimethylsilyl group or a tert-butyldimethylsilyl group. Particularly preferred are a 2-propenyloxycarbonyl group, a tert-butoxycarbonyl group and a p-nitrobenzyloxycarbonyl group.

The compounds of the present invention are characterized in that they have an amino group substituted by at least one lower alkyl group (a secondary or tertiary amino group or an ammonio group) at the terminal of the $C_{2-4}$ alkylene group of the side chain at the 2-position of the pyrrolidinyl group substituted at the 2-position of the carbapenem structure.

When both $R^3$ and $R^4$ are lower alkyl groups, such lower alkyl groups may be the same or different.

X is a group of $-N(R^3)R^4$ (wherein $R^3$ is a lower alkyl group, and $R^4$ is a hydrogen atom or a lower alkyl group) or a group of $-N^+(R^5)(R^6)R^7$ (wherein each of $R^5$ $R^6$ and $R^7$ which may be the same or different, is a lower alkyl group). X may, for example, be an N-methylamino group, an N-ethylamino group, an N-propylamino group, an N-isopropylamino group, an N-butylamino group, an N,N-dimethylamino group, an N,N-diethylamino group, an N,N-dipropylamino group, an N,N-diisopropylamino group, an N,N-dibutylamino group, an N-ethyl-N-methylamino group, an N-methyl-N-propylamino group, an N-ethyl-N-propylamino group, an N,N,N-trimethylammonio group, an N,N,N-triethylammonio group, an N,N-dimethyl-N-ethylammonio group or an N,N-diethyl-N-methylammonio group, preferably an N-methylamino group, an N-ethylamino group, an N,N-dimethylamino group, an N,N-diethylamino group or an N,N,N-trimethylammonio group.

$R^2$ is a hydrogen atom or a negative charge. When the side chain at the 2-position of the pyrrolidinyl group forms an ammonio group, $R^2$ is a negative charge and forms a pair together with the ammonium ion, whereby the compound of the formula (I) forms an intramolecular salt.

The salt of the compound of the formula (I) is a common pharmaceutically acceptable salt and may, for example, be a salt at the carboxyl group at the 3-position of the carbapenem structure, or at the pyrrolidine base or the base on the side chain substituted on the pyrrolidine ring.

The basic addition salt at said carboxyl group includes, for example, an alkali metal salt such as a sodium salt or a potassium salt; an alkaline earth metal salt such as a calcium salt or a magnesium salt; an ammonium salt;

an aliphatic amine salt such as a trimethylamine salt, a triethylamine salt, a dicyclohexylamine salt, an ethanolamine salt, a diethanolamine salt, a triethanolamine salt or a procaine salt; an aralkylamine salt such as an N,N'-dibenzylethylenediamine salt; an aromatic heterocyclic amine salt such as a pyridine salt, a picoline salt, a quinoline salt or an isoquinoline salt; a quaternary ammonium salt such as a tetramethylammonium salt, a tetraethylammonium salt, a benzyltrimethylammonium salt, a benzyltriethylammonium salt, a benzyltributylammonium salt, a methyltrioctylammonium salt or a tetrabutylammonium salt; and a basic amino acid salt such as an arginine salt or a lysine salt.

The acid addition salt at the pyrrolidine base or at the base on the side chain substituted on the pyrrolidine ring includes, for example, an inorganic salt such as a hydrochloride, a sulfate, a nitrate, a phosphate, a carbonate, a hydrogencarbonate or a perchlorate; an organic salt such as an acetate, a propionate, a lactate, a maleate, a fumarate, a tartrate, a malate, a succinate or an ascorbate; a sulfonate such as a methanesulfonate, an isethionate, a benzenesulfonate or a p-toluenesulfonate; and an acidic amino acid salt such as an aspartate or a glutamate.

The non-toxic ester of the compound of the formula (I) means a common pharmaceutically acceptable ester at the carboxyl group at the 3-position of the carbapenem structure. For example, it includes an ester with an alkanoyloxymethyl group such as an acetoxymethyl group or a pivaloyloxymethyl group, an ester with an alkoxycarbonyloxyalkyl group such as a 1-(ethoxycarbonyloxy)ethyl group, an ester with a phthalidyl group and an ester with a (5-substituted-2-oxo- 1,3-dioxol-4-yl)methyl group such as a (5-methyl-2-oxo-1,3-dioxol-4-yl)methyl group.

Among the compounds of the formula (I), preferred is (5R,6S)-6-[(R)-1-hydroxyethyl]-2-[(2R,4S)-2-[2-(methylamino)ethyl]pyrrolidin-4-ylthio]-1-carbapen-2-em-3-carboxylic acid, (1R,5S,6S)-6-[(R)-1-hydroxyethyl]-1-methyl-2-[(2R,4S)-2-[2-(methylamino)ethyl]pyrrolidin-4-ylthio]-1-carbapen-2-em-3-carboxylic acid, (5R,6S)-2-[(2R,4S)-2-[2-(dimethylamino)ethyl]pyrrolidin-4-ylthio]-6-[(R)-1-hydroxyethyl]-1-carbapen-2-em-3-carboxylic acid, (1R,5S,6S)-2-[(2R,4S)-2-[2-(dimethylamino)ethyl]pyrrolidin-4-ylthio]-6-[(R)-1-hydroxyethyl]-1-methyl-1-carbapen-2-em-3-carboxylic acid, (5R,6S)-6-[(R)-1-hydroxyethyl]-2-[(2R,4S)-2-[3-(methylamino)propyl]pyrrolidin-4-ylthio]-1-carbapen-2-em-3-carboxylic acid or (1R,5S,6S)-6-[(R)-1-hydroxyethyl]-1-methyl-2-[(2R,4S)-2-[3-(methylamino)propyl]pyrrolidin-4-ylthio]-1-carbapen-2-em-3-carboxylic acid. Among these, particularly preferred is (1R,5S,6S)-6-[(R)-1-hydroxyethyl]-1-methyl-2-[(2R,4S)-2-[2-(methylamino)ethyl]pyrrolidin-4-ylthio]-1-carbapen-2-em-3-carboxylic acid, (1R,5S,6S)-2-[(2R,4S)-2-[2-(dimethylamino)ethyl]-pyrrolidin-4-ylthio]-6-[(R)-1-hydroxyethyl]-1-methyl-1-carbapen-2-em-3-carboxylic acid or (1R,5S,6S)-6-[(R)-1-hydroxyethyl]-1-methyl-2-[(2R,4S)-2-[3-(methylamino)propyl]pyrrolidin-4-ylthio]-1-carbapen-2-em-3-carboxylic acid. Especially preferred is (1R,5S,6S)-6-[(R)-1-hydroxyethyl]-1-methyl-2-[(2R,4S)-2-[2-(methylamino)ethyl]pyrrolidin-4-ylthio]-1-carbapen-2-em-3-carboxylic acid or (1R,5S,6S)-6-[(R)-1-hydroxyethyl]-1-methyl-2-[(2R,4S)-2-[3-(methylamino)propyl]pyrrolidin-4-ylthio]-1-carbapen-2-em-3-carboxylic acid.

Now, the process for producing the compound of the present invention will be described.

An activating reagent is reacted to a compound of the formula:

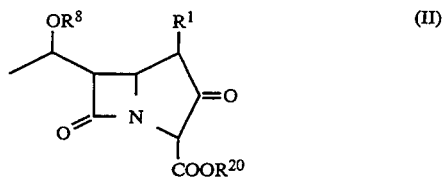

wherein $R^1$ is a hydrogen atom or a methyl group, $R^8$ is a hydrogen atom or a hydroxyl-protecting group, and $R^{20}$ is a hydrogen atom or a carboxyl-protecting group, in an inert organic solvent in the presence of a base to form a reactive derivative of the formula (II'):

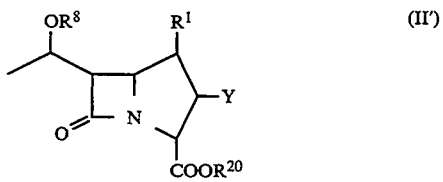

wherein $R^1$, $R^8$ and $R^{20}$ are as defined above, and Y is a leaving group.

The inert organic solvent to be used for the reaction may, for example, be diethyl ether, tetrahydrofuran, dioxane, benzene, toluene, chlorobenzene, methylene chloride, chloroform, carbon tetrachloride, dichloroethane, trichloroethylene, acetone, ethyl acetate, acetonitrile, N,N-dimethylformamide, hexamethylphosphoric triamide or a mixture of such solvents. Particularly preferred are acetonitrile and benzene.

The base to be used for the reaction may, for example, be a tertiary aliphatic amine such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) or 1,5-diazabicyclo[4.3.0]non-5-ene (DBN); or an aromatic amine such as pyridine, 4-dimethylaminopyridine, picoline, lutidine, quinoline or isoquinoline. Particularly preferred are N,N-diisopropylethylamine and triethylamine.

The activating reagent to be used for the reaction may, for example, be an acid anhydride such as trifluoroacetic anhydride, methanesulfonic anhydride, trifluoromethanesulfonic anhydride or p-toluenesulfonic anhydride; or an acid chloride such as methanesulfonyl chloride, p-toluenesulfonyl chloride or diphenyl chlorophosphate. Particularly preferred is diphenyl chlorophosphate.

In the formula (II'), Y is a leaving group such as a trifluoroacetoxy group, a methanesulfonyloxy group, a trifluoromethanesulfonyloxy group, a p-toluenesulfonyloxy group or a diphenoxyphosphoryloxy group. Particularly preferred is a diphenoxyphosphoryloxy group.

For the reaction, from 1 to 3 mols, preferably from 1 to 1.5 mols, of the base and from 1 to 1.2 mols of the activating reagent are used per mol of the compound of the formula (II).

The reaction is conducted usually within a temperature range of from −40° to 50° C., preferably from −20° to 20° C., and usually completed quantitatively in from 0.5 to 3 hours.

After completion of the reaction, the reaction product is treated in accordance with a usual method to obtain the reactive derivative (II') of the compound of the formula (II) quantitatively.

The reaction of the reactive derivative of the formula (II') with a compound of the formula:

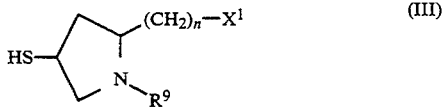

(III)

wherein $R^9$ is a hydrogen atom or an imino-protecting group, $X^1$ is a group of the formula —$N(R^3)R^{40}$ (wherein $R^3$ is a lower alkyl group, and $R^{40}$ is a hydrogen atom, a lower alkyl group or an imino-protecting group) or a group of —$N^+(R^5)(R^6)R^7$ (wherein each of $R^5$, $R^6$ and $R^7$ which may be the same or different, is a lower alkyl group), and n is an integer of from 2 to 4, is conducted using the above-mentioned inert organic solvent and base to form a compound of the formula:

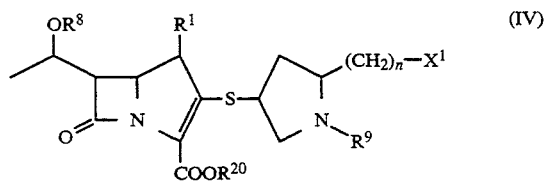

(IV)

wherein $R^1$, $R^8$, $R^9$, $R^{20}$, $X^1$ and n are as defined above

The reaction is conducted using from 1 to 2 mols, preferably from 1 to 1.5 mols, of the base and from 1 to 1.2 mols of the compound of the formula (III), per mol of the reactive derivative of the formula (II'). The reaction is conducted usually within a temperature range of from —40° to 50° C., preferably from —20° to 20° C., and the reaction is completed usually in from 0.5 to 3 hours.

Further, the compound of the formula (IV) can be prepared in one step from the compound of the formula (II). Namely, without isolating the reactive derivative of the formula (II') prepared from the compound of the formula (II), the compound of the formula (III) is reacted thereto in the same reaction system to prepare the compound of the formula (IV) efficiently. To conduct the production in one step, from 2 to 4 mols, preferably from 2.5 to 3.5 mols, of the base is employed per mol of the compound of the formula (II).

After completion of the reaction, usual treatment is conducted to obtain a crude product of the formula (IV), which may be subjected to a reaction for removing a protecting group without purification. However, it is preferred to purify the crude product (IV) by crystallization or by column chromatography by means of e.g. silica gel.

From the compound of the formula (IV) thus obtained, a compound of the formula (I) can be obtained, if necessary, by conducting a reaction for removing a protecting group for a hydroxyl group, an imino group and a carboxyl group.

For the removal of the protecting groups, the method varies depending upon the type of the protecting groups. However, the removal can be conducted in accordance with conventional methods, for example, by solvolysis, by chemical reduction or by hydrogenation.

For example, when in the above formula (IV), the protecting group for the hydroxyl group and/or for the imino group is an aralkyloxycarbonyl group such as a benzyloxycarbonyl group or a p-nitrobenzyloxycarbonyl group, and the protecting group for the carboxyl group is an aralkyl group such as a benzyl group, a p-nitrobenzyl group or a benzhydryl group, such protecting groups can be removed by catalytic hydrogenation by means of a platinum catalyst such as platinum oxide, platinum wire or platinum black, or a palladium catalyst such as palladium black, palladium oxide, palladium-carbon or palladium hydroxide-carbon.

As a solvent to be used for such a catalytic hydrogenation reaction, methanol, ethanol, tetrahydrofuran, dioxane, acetic acid or a solvent mixture of such an organic solvent with water or with a buffer solution of e.g. a phosphate, may be used.

The reaction can be completed in from 0.5 to 4 hours at a temperature within a range of from 0° to 50° C. under hydrogen gas stream of from 1 to 4 atm.

When in the above formula (IV), the protecting group for the hydroxyl group and/or the imino group is an allyloxycarbonyl group, and the protecting group for the carboxyl group is an allyl group, such protecting groups can be removed by reacting an organo-soluble palladium complex catalyst in an inert organic solvent containing an allyl group-capturing agent (method by W. McCombie et al., J. Org. Chem., vol. 47, p. 587–590 (1982) and method by F. Guibé, the same literature, vol. 52, p. 4,984–4,993 (1987)).

The solvent useful for the reaction includes, for example, water, acetone, diethyl ether, tetrahydrofuran, dioxane, ethyl acetate, acetonitrile, methylene chloride, chloroform and a solvent mixture thereof.

The palladium compound complex useful for this reaction includes, for example, palladium-carbon, palladium hydroxide-carbon, palladium(II) chloride, palladium(II) acetate, tetrakis(triphenylphosphine)palladium (O), tetrakis(triphenoxyphosphine)palladium (O), tetrakis(triethoxyphosphine)palladium (O), bis[ethylenebis(diphenylphosphine)]palladium (O), tetrakis[tri(2-furyl)phosphine]palladium (O), bis(triphenylphosphine)palladium(II) chloride and bis(triphenylphosphine)palladium(II) acetate.

The allyl group-capturing agent may, for example, be dimedone, formic acid, acetic acid, ammonium formate, sodium formate, sodium 2-ethylhexanoate, potassium 2-ethylhexanoate, pyrrolidine, piperidine and tributyltin hydride.

The reaction is conducted usually within a temperature range of from —10° to 50° C., preferably from 0° to 30° C. using from 0.01 to 0.5 mol of the catalyst and from 1 to 6 mols of the allyl group-capturing agent relative to 1 mol of the compound of the formula (IV), and the reaction is completed usually in from 0.5 to 3 hours.

Further, when in the above formula (IV), the protecting group for the hydroxyl group and/or the imino group is an o-nitrobenzyloxycarbonyl group, and the protecting group for the carboxyl group is an o-nitrobenzyl group, such protecting groups can be removed by a photo reaction (method by Amit et al., J. Org. Chem., vol. 39, p. 192–196 (1974)).

After completion of the reactions for removing the protecting groups, the compound of the formula (I) can be isolated by usual treatment such as column chromatography using silica gel or adsorptive resin, freeze-drying or crystallization.

Further, when the protecting group for the carboxyl group at the 3-position of the compound of the formula (IV) is a lower alkanoyloxyalkyl group such as an acetoxymethyl group or a pivaloyloxymethyl group, a methoxymethyl group, an indanyl group or a phthalidyl group, such an ester will be physiologically hydrolyzed in vivo. Therefore, such a compound can directly be administered to a human being or to an animal without preliminarily removing the protecting group.

The compound of the formula (I) can be converted to a pharmaceutically acceptable salt or ester by a conventional method.

The starting material of the formula (II) can be prepared, for example, by a method by Salzmann et al. when $R^1$ is a hydrogen atom (J. Am. Chem. Soc., vol. 102, p.6161–6163 (1981)) or by a method by Shih et al. when $R^1$ is a methyl group (Heterocycles, vol. 21, p.29–40 (1984)).

The starting material of the formula (III) can be synthesized by the following method.

The hydroxyl group of the compound 1 is activated by a usual method, and a thioacetate such as potassium thioacetate is reacted thereto to convert it to an acetylthio derivative 3, followed by alkali or acid hydrolysis to obtain a thiol derivative of the formula (III).

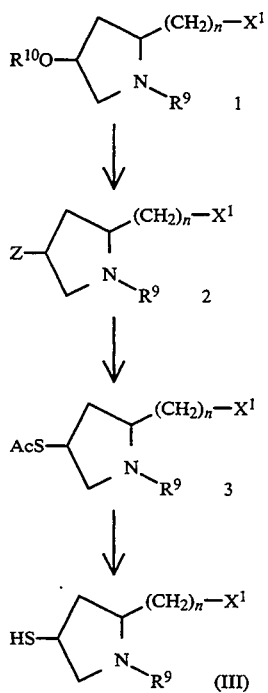

In the above formulas, $R^{10}$ is a hydrogen atom or a hydroxyl-protecting group, Z is a leaving group selected from the group consisting of a chlorine atom, a bromine atom, an iodine atom, a trifluoroacetoxy group, a methanesulfonyloxy group, a trifluoromethanesulfonyloxy group and a p-toluenesulfonyloxy group, Ac is an acetyl group, and $R^9$, $X^1$ and n are as defined above.

A group of compounds having the formula 1 can be prepared in accordance with the methods described in the Reference Examples.

The compounds of the present invention exhibit strong antibacterial activities against various gram positive bacteria and gram negative bacteria.

To demonstrate the usefulness of the compounds of the present invention, the in vitro antibacterial activities against bacteria were measured by the following agar plate dilution method (standard method by Japan Chemotherapy Society, Chemotherapy, vol. 29, p. 76–79 (1981)). One platinum loopful of each test microorganism incubated overnight in Mueller Hinton broth, was inoculated to Mueller Hinton agar (inoculum size: $10^6$ CFU/ml). Such culture media contained antibacterial agents in various concentrations. After incubation at 37° C. for 16 hours, the minimum inhibitory concentrations (MIC: μg/ml) were measured. Further, the DHP-I susceptibility was quantitatively analyzed by the method by Kropp et al. (Antimicrob. Agents Chemother., vol. 22, p. 62–70 (1982)), whereby the smaller the numerical value representing the ratio to imipenem (=1.0), the higher the stability.

The minimum inhibitory concentrations and the DHP-I susceptibility of the compounds of the present invention were compared with imipenem and the compound of REFERENCE EXAMPLE 4. The results are shown in Table 1.

TABLE 1

| Minimum Inhibitory Concentration (MIC: μg/ml) and DHP-I Susceptibility | | | | |
|---|---|---|---|---|
| Test microorganism | Example 1 | Example 3 | Reference Example 1 | Imipenem |
| P. aeruginosa MB5002 | 0.78 | 0.78 | 6.25 | 1.56 |
| P. aeruginosa MB5178 | 3.13 | 3.13 | 12.5 | 25 |
| DHP-I susceptibility | <0.05 | 0.07 | 0.7 | 1.0 |

The compounds of the present invention have excellent antibacterial activities against various gram positive bacteria and gram negative bacteria and are useful as antibacterial agents for the treatment and prevention of the human infectious diseases caused by such bacteria. Typical pathogens sensitive to the antibacterial agents of the present invention include, for example, species of genus Staphylococcus, genus Enterococcus, genus Escherichia, genus Enterobacter, genus Klebsiella, genus Serratia, genus Proteus and genus Pseudomonas. The compounds of the present invention exhibit excellent antibacterial activities particularly against Methicillin resistant *Staphylococcus aureus* and against thienamycin resistant *Pseudomonas aeruginosa*.

The compounds of the present invention are very stable against DHP-I although the stability varies depending upon the individual compounds, and they are excellent also in the physicochemical stability and in the solubility in water.

The compounds of the present invention may be used in the form of drug formulations suitable for non-oral administration, oral administration or external administration, by mixing them with carriers of solid or liquid excipients known in this field. The main administration route is non-oral (intravenous or intramuscular injection) administration by injection or local administration. Drug formulations include liquid formulations such as injection solutions, syrups or emulsions, solid formulations such as tablets, capsules or granules, and external application formulations such as ointments or suppositories. These formulations may contain additives such as a base, an assisting agent, a stabilizer, a wetting agent, an emulsifier, an absorption-promoting agent, a surfactant, etc. which are commonly employed, as the case requires.

The additives include, for example, distilled water for injection, Ringer's solution, glucose, sucrose syrup, gelatin, edible oil, cacao butter, ethylene glycol, sucrose, corn starch, magnesium stearate and talc.

The dose varies depending upon the condition of the patient, the weight, the age, the sex, the type of formulation, the number of administration times, etc. Usually, however, a preferred daily dose of the active ingredient to an adult is from about 5 to 50 mg/kg, and a preferred daily dose to a child is within a range of from about 5 to 25 mg/kg, which is preferably administered once a day or in a few times a day.

The compound of the present invention may be administered in combination with a DHP-I inhibiting agent such as cilastatin [sodium (Z)-7-(L-amino-2-carboxyethylthio)-2-(2,2-dimethylcyclopropanecarboxamide)-2-heptenoate] (Japanese Unexamined Patent Publication No. 81518/1981; European Patent No. 28,778; J. Med. Chem., vol. 30, p. 1074 (1987)).

Now, the present invention will be described in further detail with reference to Examples and Reference Examples. However, it should be understood that the present invention is by no means restricted by such specific Examples.

In the thin layer chromatography in the Examples and Reference Examples, silica gel 60F$_{245}$ (Merck) was used as the plate, and an ultraviolet detector was used as a detecting device. As the silica gel for the column, Wakogel TM C-300 (Wako Junyaku) was used, and as the silica gel for reversed phase column, LC-SORB TM SP-B-ODS (Chemco) or YMC-GEL TM ODS-AQ 120-S50 (Yamamura Chemical Laboratories) was used. As the high pressure liquid chromatograph, JASCO 800 series (Nippon Bunko) was used. When the NMR spectrum was measured using a dimethyl sulfoxide-d$_6$ or chloroform-d solution, tetramethylsilane (TMS) was used as the internal standard, and when measured using a deuterium oxide solution, 2,2-dimethyl-2-silapentane-5-sulfonate (DSS) was used as the internal standard, and the measurement was conducted by means of XL-200 (200 MHz;Varian) model spectrometer. All δ values are shown by ppm.

The meanings of the abbreviations used for the NMR measurement are as follows:

s: singlet
d: doublet
t: triplet
q: quartet
ABq: AB-type quartet
dd: double doublet
m: multiplet
br: broad
J: coupling constant
Hz: hertz
CDCl$_3$: chloroform-d
D$_2$O: deuterium oxide The meanings of the abbreviations used in the reaction formulas are as follows:

Ac: acetyl group
Alloc: allyloxycarbonyl group
Boc: tert-butoxycarbonyl group
Me: methyl group
Ms: methanesulfonyl group
PNB: p-nitrobenzyl group
PNZ: p-nitrobenzyloxycarbonyl group
TBS: tert-butyldimethylsilyl group Tr: triphenylmethyl group

EXAMPLE 1

(1R,5S,6S)-6-[(R)-1-Hydroxyethyl]-1-methyl-2-[(2R,4S)-2-[2-(methylamino)ethyl]pyrrolidin-4-ylthio]-1-carbapen-2-em-3-carboxylic Acid

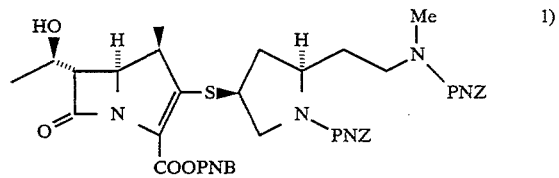

To a solution of (2R,4S)-4-acetylthio-2-[2-(N-methyl-N-p-nitrobenzyloxycarbonylamino)ethyl]-N-p-nitrobenzyloxycarbonylpyrrolidine prepared in REFERENCE EXAMPLE 1 (240 mg, 0.428 mmol) in methanol (17 ml) was dropwise added 1N aqueous sodium hydroxide (0.43 ml, 0.43 mmol) under a nitrogen atmosphere, and the mixture was stirred at room temperature for 15 minutes. The reaction solution was acidified by an addition of 1N hydrochloric acid (0.47 ml, 0.47 mmol), and the solvent was removed in vacuo. To the residue was added ethyl acetate (30 ml), and the mixture was washed successively with water and saturated aqueous sodium chloride and dried over anhydrous sodium sulfate. The solvent was removed in vacuo to give a crude thiol.

To an ice-cooled solution of p-nitrobenzyl (1R,5S,6S)-2-diphenoxyphosphoryloxy-6-[(R)-1-hydroxyethyl]-1-methyl-1-carbapen-2-em-3-carboxylate (240 mg, 0.4 mmol) in acetonitrile (6 ml) were dropwise successively added diisopropylethylamine (0.09 ml, 0,517 mmol) and a solution of the crude thiol in acetonitrile (2 ml) under a nitrogen atmosphere, and the mixture was stirred at the same temperature for 2 h and at 5° C. overnight. To the reaction solution was added ethyl acetate (30 ml), and the mixture was washed successively with water and saturated aqueous sodium chloride and dried over anhydrous sodium sulfate. The solvent was removed in vacuo, and the residue was subjected to silica gel column chromatography (Wakogel TM C-300, chloroform-methanol) to give p-nitrobenzyl (1R,5S,6S)-6-[(R)-1-hydroxyethyl]-1-methyl-2-[(2R,4S)-2-[2-(N-methyl-N-p-nitrobenzyloxycarbonylamino)ethyl]-N-p-nitrobenzyloxycarbonylpyrrolidin-4-ylthio]-1-carbapen-2-em-3-carboxylate (290 mg, yield: 83%).

IR(KBr)cm$^{-1}$:
3450,1775,1705,1605,1520,1345,1210,1135,850, 740
NMR(CDCl$_3$) δ: 1.27(3H,d,J=7 Hz), 1.38(3H,d,J=7 Hz), 1.45–1.85(4H,m), 2.5–2.75(1H,m), 2.88 & 2.98(total 3H, each s), 3.0–3.45(5H,m), 3.45–3.7(1H,m), 3.8–4.05(2H,m), 4.1–42.5 (2H,m), 5.0–5.6(6H,m), 7.53(4H,d,J=9 Hz), 7.67(2H,d,J=9 Hz), 8.24(6H,d,J=9 Hz)

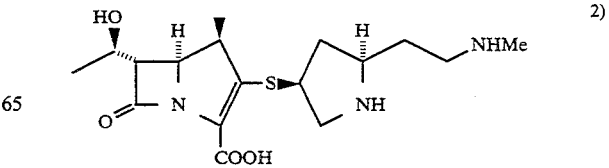

10% Palladium-carbon (280 mg) was suspended in a 0.1M 3-morpholinopropane sulfonate buffer solution (pH 7.0, 5 ml), and the suspension was stirred under atmospheric pressure under a hydrogen atmosphere for 30 minutes. Then, the catalyst was collected by filtration and washed with water.

This catalyst was added to a mixture of a solution of the above compound (250 mg, 0.290 mmol) in tetrahydrofuran (20 ml)-0.1M 3-morpholinopropane sulfonate buffer (pH 7.0, 20 ml)-ethanol (3.2 ml). The mixture was stirred under atmospheric pressure under a hydrogen atmosphere at room temperature for 2 h. The catalyst was filtered off, and tetrahydrofuran and ethanol were removed in vacuo. The residue was washed with ethyl acetate. Insoluble material was filtered off, and the filtrate was concentrated in vacuo. The residue was purified by reverse phase column chromatography (Chemco LC-SORB TM, SP-B-ODS, 0-30% methanol in water) and lyophilized to give the title compound (60 mg, yield: 56%).

IR(KBr)cm$^{-1}$: 3450,1755,1595,1395,1255 NMR(D$_2$O) δ: 1.18(3H,d,J=7 Hz), 1.26(3H,d,J=6 Hz), 1.38(1H,m), 1.8–2.1(2H,m), 2.45–2.75(2H,m), 2.69(3H,s), 2.8–3.15(3H,m), 3.15–3.45(3H,m), 3.77(1H,m), 4.1–4.3(2H,m) UVλ$_{max}$ (0.1M 3-morpholinopropane sulfonate buffer, pH 7.0): 299 nm (ε=7500)

EXAMPLE 2

(1R,5S,6S)-2-[(2R,4S)-2-[2-(Dimethylamino)ethyl]-pyrrolidin-4-ylthio]-6-[(R)-1-hydroxyethyl]-1-methyl-1-carbapen-2-em-3-carboxylic Acid

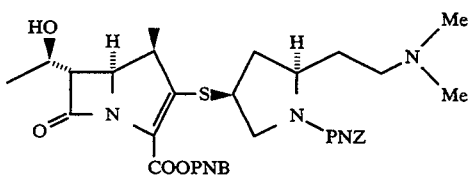

To an ice-cooled solution of (2R,4S)-2-[2-(dimethylamino)ethyl]-N-p-nitrobenzyloxycarbonyl-4-(triphenylmethylthio)pyrrolidine prepared in REFERENCE EXAMPLE 2 (130 mg, 0.218 mmol) in methylene chloride (0.5 ml) was added trifluoroacetic acid (0.5 ml) under a nitrogen atmosphere. Triethylsilane (0.04 ml, 0.250 mmol) was dropwise added thereto, and the mixture was stirred at the same temperature for 20 minutes. The reaction solution was distilled in vacuo. Then, to the residue was added ethyl acetate (30 ml), and the mixture was washed successively with 1M phosphoric acid buffer (pH 5.5), water and saturated aqueous sodium chloride, and dried over anhydrous sodium sulfate. The solvent was removed in vacuo, and the residue was subjected to silica gel column chromatography (Wakogel TM C-300, chloroform-methanol) to obtain a thiol.

Using this thiol and p-nitrobenzyl (1R,5S,6S)-2-diphenoxyphosphoryloxy-6-[(R)-1-hydroxyethyl]-1-methyl-1-carbapen-2-em-3-carboxylate (140 mg, 0.235 mmol), the same reaction as in EXAMPLE 1-1 was conducted to obtain p-nitrobenzyl (1R,5S,6S)-2-[(2R,4S)-2-[2-(dimethylamino)ethyl]-N-p-nitrobenzyloxycarbonylpyrrolidin-4-ylthio]-6-[(R)-1-hydroxyethyl]-1-methyl-1-carbapen-2-em-3-carboxylate (100 mg, yield: 66%).

IR(KBr)cm$^{-1}$: 3440,1775,1705,1605,1345,1210,1135,1110,850, 740

NMR(CDCl$_3$) δ: 1.29(3H,d,J=7 Hz), 1.37(3H,d,J=6 Hz), 1.5–2.2(4H,m), 2.4(1H,m), 2.65(6H,s), 2.75–3.05(2H,m), 3.15–3.5(3H,m), 3.68(1H,m), 3.8–4.35(4H,m), 5.15–5.6(6H,m), 7.45–7.75 (6H,m), 8.15–8.35(6H,m)

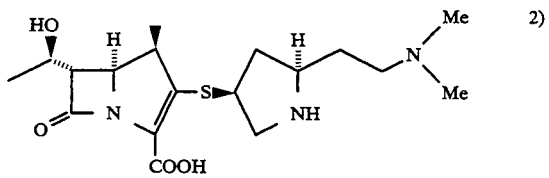

Using the above compound (100 mg, 0,143 mmol), the same reaction as in EXAMPLE 1-2 was conducted to obtain the title compound (6 mg, yield: 11%).

IR(KBr)cm$^{-1}$: 3430,1750,1600,1395 NMR(D$_2$O) δ: 1.18(3H,d,J=7 Hz), 1.25(3H,d,J=6 Hz), 1.4(1H,m), 1.8–2.7(4H,m), 2.65(6H,s), 2.8–3.45(6H,m), 3.8(1H,m), 4.1–4.3(2H,m) UVλ$_{max}$ (0.1M 3-morpholinopropane sulfonate buffer, pH 7.0): 298 nm (ε=7000)

EXAMPLE 3

(1R,5S,6S)-6-[(R)-1-Hydroxyethyl]-1-methyl-2-[(2R,4S)-2-[3-(methylamino)propyl]pyrrolidin-4-ylthio]-1-carbapen-2-em-3-carboxylic acid Monohydrochloride

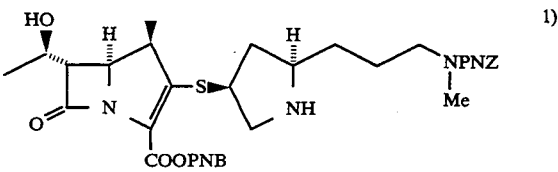

Using (2R,4S)-4-acetylthio-2-[3-(N-methyl-N-p-nitrobenzyloxycarbonylamino)propyl]-N-p-nitrobenzyloxycarbonylpyrrolidine prepared in REFERENCE EXAMPLE 3 (7.85 g, 13.66 mmol) and p-nitrobenzyl (1R,5S,6S)-2-diphenoxyphosphoryloxy-6-[(R)-1-hydroxyethyl]-1-methyl-1-carbapen-2-em-3-carboxylate (8.12 g, 13.66 mmol), the same reaction as in EXAMPLE 1-1 was conducted to obtain p-nitrobenzyl (1R,5S,6S)-6-[(R)-1-hydroxyethyl]-1-methyl-2-[(2R,4S)-2-[3-(N-methyl-N-p-nitrobenzyloxycarbonylamino)propyl]-N-p-nitrobenzyloxycarbonylpyrrolidin-4-ylthio]-1-carbapen-2-em-3-carboxylate (9.23 g, yield: 7%).

IR(KBr)cm$^{-1}$: 3430,1770,1700,1605,1520,1400,1345,1205, 1135,1105,850,735 NMR (CDCl$_3$) δ: 1.27(3H,d,J=7 Hz), 1.37(3H,d,J=6 Hz), 1.4–2.1(8H,m), 2.55(1H,m), 2.94(3H,s), 3.15–3.45(3H,m), 3.6(1H,m), 3.9–4.2(2H,m), 4.26(2H,m), 5.15–5.6(6H,m), 7.51(4H,d,J=9 Hz), 7.65(2H,d,J=9 Hz), 8.21(6H,d,J=9 Hz)

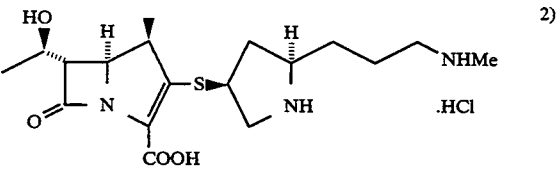

Using the above compound (9.06 g, 10.33 mmol), the same reaction as in EXAMPLE 1-2 was conducted, and the eluate after purification was adjusted to pH 6.5 with 1N hydrochloric acid, concentrated and lyophilized to give the title compound (3.09 g, yield: 71%).

IR(KBr)cm$^{-1}$:
3420,2970,1760,1590,1455,1390,1285,1255,1145
NMR(D$_2$) δ: 1.19(3H,d,J=7 Hz), 1.26(3H,d,J=6 Hz), 1.6–2.0(6H,m), 2.70(3H,s), 2.76(1H,m), 3.07(2H,m), 3.3–3.5(2H,m), 3.6–3.8(2H,m), 4.0(1H,m), 4.22(2H,m)
UVλ$_{max}$ (0.1M 3-morpholinopropane sulfonate buffer, pH 7.0): 298 nm (ε=7300)

REFERENCE EXAMPLE 1

(2R,4S)-4-Acetylthio-2-[2-(N-methyl-N-p-nitrobenzyloxy-carbonylamino)ethyl-]-N-p-nitrobenzyloxycarbonyl-pyrrolidine

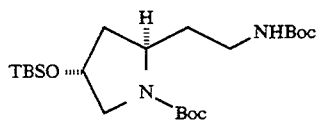
1)

To an ice-cooled suspension of aluminum lithium hydride (380 mg, 10 mmol) in diethyl ether (20 ml) was dropwise added a solution of (2R,4R)-N-tert-butoxycarbonyl-4-tert-butyldimethylsiloxy-2-cyanomethylpyrrolidine (3.36 g, 9.87 mmol) in diethyl ether (5 ml) under a nitrogen atmosphere, and the mixture was stirred at the same temperature for 1 h. While vigorously stirring the mixture under cooling with ice, water (0.4 ml), 20% aqueous sodium hydroxide (0.3 ml) and water (1.4 ml) were added successively. The mixture was stirred for a while. To the reaction solution was added diethyl ether (50 ml), and insoluble material was removed. This insoluble material was washed with diethyl ether (50 ml×2). The ether solutions were put together, and the mixture was washed successively with water and saturated aqueous sodium chloride, and dried over anhydrous sodium sulfate. The solvent was removed in vacuo to obtain a crude amine.

To a solution of this crude amine in dioxane (20 ml) was added S-tert-butoxycarbonyl-4,6-dimethyl-2-mercaptopyrimidine (2.40 g, 9.99 mmol), and the mixture was stirred at room temperature for 2 h. To the reaction solution was added ethyl acetate (200 ml), and the mixture was washed successively with 1N aqueous potassium hydrogensulfate, water and saturated aqueous sodium chloride, and dried over anhydrous sodium sulfate. The solvent was removed in vacuo, and the residue was subjected to silica gel column chromatography (Wakogel ™ C-300, hexane-ethyl acetate) to give (2R,4R)-N-tert-butoxycarbonyl-2-[2-(tert-butoxycarbonylamino)ethyl]-4-tert-butyldimethylsiloxypyrrolidine (3.01 g, yield: 69%).

IR(KBr)cm$^{-1}$:
3350,2920,1695,1500,1390,1365,1250,1165, 1115,835,775
NMR(CDCl$_3$) δ: 0.05(6H,s), 0.86(9H,s), 1.44(9H,s), 1.47(9H,s), 1.5–2.1(4H,m), 2.9–3.5(4H,m), 3.85–4.1(1H,m), 4.34(1H,m), 5.35(1H,m)

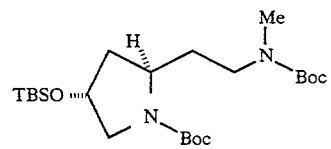
2)

To an ice-cooled solution of the above compound (1.34 g, 3.01 mmol) in N,N-dimethylformamide (10 ml) was added 60% oily sodium hydride (240 mg, 6 mmol) under a nitrogen atmosphere, and the mixture was stirred at the same temperature for 30 minutes. To the reaction solution was dropwise added methyl iodide (1.3 ml, 15.44 mmol), and the mixture was stirred under cooling with ice for 1 h and then at room temperature for 3 h. The reaction solution was poured into a mixture of ice water (100 ml) and 1N aqueous potassium hydrogensulfate (10 ml), and extracted with ethyl acetate (50 ml×3). The organic layers were put together, washed successively with 10% aqueous sodium sulfite, water and saturated aqueous sodium chloride, and dried over anhydrous sodium sulfate. The solvent was removed in vacuo, and the residue was subjected to silica gel column chromatography (Wakogel ™ C-300, hexane-ethyl acetate) to give (2R,4R)-N-tert-butoxycarbonyl-2-[2-(N-tert-butoxycarbonyl-N-methylamino)ethyl]-4-tert-butyldimethylsiloxypyrrolidine (1.31 g, yield: 95%).

IR(KBr)cm$^{-1}$:
2930,1700,1395,1365,1255,1165,1110,835,775
NMR(CDCl$_3$) δ:
0.05(6H,S), 0.86(9H,S), 1.45(9H,s), 1.46(9H,S), 1.6–1.85(2H,m), 1.95–2.2(2H,m), 2.86(3H,s), 3.1–3.5(4H,m), 3.86(1H,m), 4.32(1H,m)

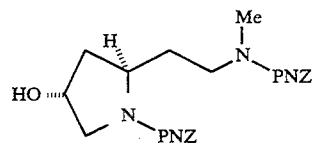
3)

To the above compound (1.31 g, 2.86 mmol) was added trifluoroacetic acid (10 ml), and the mixture was stirred overnight at room temperature. Trifluoroacetic acid was removed in vacuo, and the residue was distilled a few times after an addition of benzene.

To a solution of the residue in a mixture of dioxane (6 ml)-water (2 ml) was added sodium hydrogencarbonate (2.4 g, 28.57 mmol). Then, S-p-nitrobenzyloxycarbonyl-4,6-dimethyl-2-mercaptopyrimidine (1.92 g, 6.01 mmol) was added thereto, and the mixture was stirred at room temperature for 2 h. To the reaction solution was added ethyl acetate (200 ml), and the mixture was washed successively with water, 1N aqueous potassium hydrogensulfate, water and saturated aqueous sodium chloride, and dried over anhydrous sodium sulfate. The solvent was removed in vacuo, and the residue was subjected to silica gel column chromatography (Wakogel ™ C-300, methylene chloride-ethyl acetate) to give (2R,4R)-4-hydroxy-2-[2-(N-methyl-N-p-nitroenzyloxycarbonylamino)ethyl]-N-p-nitrobenzyloxycarbonyl-pyrrolidine (1.37 g, yield: 95%).

IR(KBr)cm$^{-1}$:
3440,2940,1700,1605,1520,1400,1345,1105,855, 735
NMR(CDCl$_3$) δ:

1.5–1.95(2H,m), 2.0–2.5(2H,m), 2.88 & 3.00(total 3H, each s), 3.05–3.8(4H,m), 4.02(1H,m), 4.46(1H,m), 5.23(4H,m), 7.53(4H,d,J=9 Hz), 8.23(4H,d,J=9 Hz)

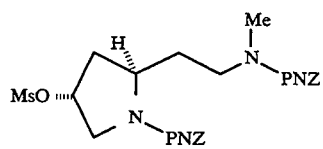
4)

To an ice-cooled solution of the obtained compound (1.37 g, 2.73 mmol) in tetrahydrofuran (10 ml) were sequentially dropwise added triethylamine (0.57 ml, 4.09 mmol) and methanesulfonyl chloride (0.30 ml, 3.88 mmol) under a nitrogen atmosphere, and the mixture was stirred under cooling with ice for 10 minutes and at room temperature for 2 h. Further, triethylamine (0.57 ml, 4.09 mmol) and then methanesulfonyl chloride (0.30 ml, 3.88 mmol) were dropwise added, and the mixture was stirred at room temperature for 1 h. To the reaction solution was added ethyl acetate (200 ml), and the mixture was washed successively with water, 1N aqueous potassium hydrogensulfate, water, saturated aqueous sodium hydrogencarbonate, water and saturated aqueous sodium chloride, and dried over anhydrous sodium sulfate. The solvent was removed in vacuo, and the residue was subjected to silica gel column chromatography (Wakogel ™ C-300, methylene chloride-ethyl acetate) to give (2R, 4R )-4-methanesulfonyloxy-2-[2-(N-methyl-N-p-nitrobenzyloxycarbonylamino)ethyl]-N-p-nitrobenzyloxycarbonylpyrrolidine (1.53 g, yield: 97%).

IR(KBr)cm$^{-1}$: 2940,1700,1605,1520,1400,1345,1170,960,900, 855,735
NMR(CDCl$_3$) δ: 1.8–2.7(4H,m), 2.8–3.05(1H,m), 2.86 & 2.99(total 3H, each br s), 3.04(3H,s), 3.15–3.7(3H,m), 3.9–4.15 (2H,m), 5.24(4H,m), 7.53 (4H,d,J=9 Hz ), 8.24(4H,d,J=9 Hz)

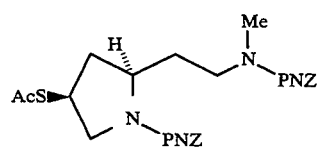
5)

To a solution of the above compound (290 mg, 0.5 mmol) in N,N-dimethylformamide (2.5 ml) were added potassium thioacetate (90 mg, 0.788 mmol) and sodium iodide (90 mg, 0.600 mmol), and the mixture was stirred under a nitrogen atmosphere at 70° C. for 5 h. The reaction solution was poured into water (30 ml) and extracted with ethyl acetate (20 ml×1, 10 ml×2). The organic layers were put together, then washed successively with 10% aqueous sodium sulfite, water and saturated aqueous sodium chloride, and dried over anhydrous sodium sulfate. The solvent was removed in vacuo, and the residue was subjected to silica gel column chromatography (Wakogel ™ C-300, hexane-ethyl acetate) to give the title compound (260 mg, yield: 93%).

IR(KBr)cm$^{-1}$: 2930,1700,1605,1520,1400,1345,1105,855,765, 740
NMR(CDCl$_3$) δ:
1.5–1.8(1H,m), 2.1–2.6(3H,m), 2.34(3H,s), 2.87 & 2.98(total 3H, each br s), 3.1–3.55(3H,m), 3.75–395(2H,m), 4.11(1H,m), 5.23(4H,s), 7.53(4H,d,J=9 Hz) , 8.24(4H,d,J=9 Hz)

REFERENCE EXAMPLE 2

(2R,4S)-2-[2-(Dimethylamino)ethyl]-N-p-nitrobenzyloxycarbonyl-4-triphenylmethylthiopyrrolidine

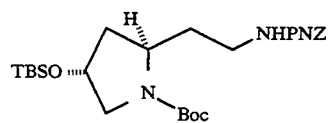
1)

A crude amine was obtained from (2R,4R)-N-tert-butoxycarbonyl-4-tert-butyldimethylsiloxy-2-cyanomethylpyrrolidine (1.70 g, 4.99 mmol) and aluminum lithium hydride (190 mg, 5 mmol) in the same manner as in

REFERENCE EXAMPLE 1-1.

To a solution of this crude amine in dioxane (15 ml) was added S-p-nitrobenzyloxycarbonyl-4,6-dimethyl-2-mercaptopyrimidine (1.60 g, 5 mmol), and the mixture was stirred at room temperature for 1 h. To the reaction solution was added ethyl acetate (200 ml), and the mixture was washed successively with 1N aqueous potassium hydrogensulfate, water and saturated aqueous sodium chloride, and dried over anhydrous sodium sulfate. The solvent was removed in vacuo, and the residue was subjected to silica gel column chromatography (Wakogel ™ C-300, hexane) to give (2R,4R)-N-tert-butoxycarbonyl-4-tert-butyldimethylsiloxy-2-[2-(p-nitrobenzyloxycarbonylamino)ethyl]pyrrolidine (2.10 g, yield: 80%).

IR(KBr)cm$^{-1}$: 2940,1730,1690,1525,1400,1350,1255,1165,840, 775
NMR (CDCl$_3$) δ: 0.05(6H,s) , 0.86(9H,s), 1.45(9H,s), 1.5–1.8(3H,m), 2.0(1H,m), 2.9–3.5(4H,m), 4.05(1H,m), 4.34(1H,m), 5.10(2H,m) , 6.10(1H,br s), 7.52(2H,d,J=9 Hz), 8.22 (2H,d,J=9 Hz )

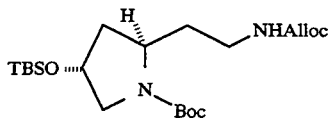
2)

To a solution of the above compound (3.39 g, 6.47 mmol) in methanol (65 ml) was added 10% palladium-carbon (350 mg), and the mixture was stirred under atmospheric pressure under a hydrogen atmosphere at room temperature for 2 h. Further, 10% palladium-carbon (350 mg) was additionally added thereto, and the mixture was stirred under atmospheric pressure under a hydrogen atmosphere at room temperature for 1 h. The catalyst was filtered off, and the filtrate was distilled under reduced pressure to remove the solvent and to obtain a crude amine.

To an ice-cooled solution of this crude amine in methylene chloride (20 ml) were successively dropwise added triethylamine (1.2 ml, 8.61 mmol) and allyl chlorocarbonate (0.82 ml, 7.73 mmol) under a nitrogen atmosphere, and the mixture was stirred at the same temperature for 1 h. To the reaction solution was added ethyl acetate (200 ml), and the mixture was washed successively with water, 1N aqueous potassium hydrogensulfate, water, saturated aqueous sodium hydrogencarbonate, water and saturated aqueous sodium chloride, and dried over anhydrous sodium sulfate. The solvent was removed in vacuo, and the residue was subjected to silica gel column chromatography (Wakogel ™ C-300, hexane-ethyl acetate) to give (2R,4R)-2-[2-(N-allyloxycarbonylamino)ethyl]-N-tert-butoxycarbonyl-4-tert-butyldimethylsiloxypyrrolidine (1.96 g, yield: 71%).

IR (KBr) cm$^{-1}$: 3350,2930,1725,1695,1510,1395,1255,1165, 1120,835,775

NMR (CDCl$_3$) δ: 0.06(6H,s), 0.86(9H,s), 1.46(9H,S), 1.55–1.85(3H,m), 1.9–2.1(1H,m), 2.9–3.55(4H,m), 3.9–4.15(1H,m), 4.36(1H,m), 4.58(2H,m), 5.15–5.4(2H,m), 5.75–6.10(2H,m)

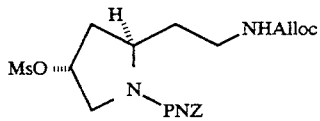
3)

To a solution of the above compound (1.17 g, 2.73 mmol) in tetrahydrofuran (10 ml) was added a 1.0M tetrabutylammonium fluoride-tetrahydrofuran solution (3.3 ml, 3.30 mmol), and the mixture was stirred at room temperature for 1 h. The solvent was removed in vacuo, and ethyl acetate (150 ml) was added to the residue. The mixture was washed successively with water, 1N aqueous potassium hydrogensulfate, water and saturated aqueous sodium chloride, and dried over anhydrous sodium sulfate. The solvent was distilled off under reduced pressure to obtain a silyl-removed product.

To this silyl-removed product was added trifluoroacetic acid (5 ml), and the mixture was stirred at room temperature for 10 minutes. Trifluoroacetic acid was distilled off under reduced pressure, and the residue was distilled a few times after an addition of benzene to obtain a crude amine.

To a solution of this crude amine in a mixture of dioxane (4.5 ml)-water (1.5 ml) were successively added sodium hydrogencarbonate (2.30 g, 27.38 mmol) and S-p-nitrobenzyloxycarbonyl-4,6-dimethyl-2-mercaptopyrimidine (880 mg, 2.76 mmol), and the mixture was stirred at room temperature overnight. To the reaction solution was added ethyl acetate (70 ml), and the mixture was washed successively with water, 1N aqueous potassium hydrogensulfate, water, saturated aqueous sodium hydrogencarbonate, water and saturated aqueous sodium chloride, and dried over anhydrous sodium sulfate. The solvent was removed in vacuo to obtain a N-protected product.

To an ice-cooled solution of this N-protected product in tetrahydrofuran (10 ml) were successively dropwise added triethylamine (0.84 ml, 6.03 mmol) and methanesulfonyl chloride (0.46 ml, 5.94 mmol) under a nitrogen atmosphere, and the mixture was stirred at the same temperature for 1 h. To the reaction solution was added ethyl acetate (60 ml), and the mixture was washed successively with water, 1N aqueous potassium hydrogensulfate, water, saturated aqueous sodium hydrogencarbonate, water and saturated aqueous sodium chloride, and dried over anhydrous sodium sulfate. The solvent was removed in vacuo, and the residue was subjected to silica gel column chromatography (Wakogel ™ C-300, hexane-ethyl acetate) to give (2R,4R)-2-[2-(N-allyloxycarbonylamino)ethyl]- 4-methanesulfonyloxy-N-p-nitrobenzyloxycarbonylpyrrolidine (1.03 g, yield: 80%).

IR(KBr)cm$^{-1}$: 3370,1695,1550,1525,1405,1350,1260,1175, 1120,965,920,910 NMR (CDCl$_3$) δ: 1.5–2.1(4H,m), 2.5(1H,m), 2.95–3.3(1H,m), 3.03(3H,s), 3.36(1H,m), 3.58(1H,m), 3.9–4.3(2H,m), 4.56(2H,m), 5.0–5.5(5H,m), 5.9(1H,m), 7.54(2H,d,J=9 Hz), 8.24(2H,d,J=9 Hz)

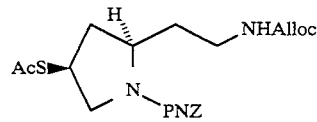
4)

(2R,4S)-4-Acetylthio-2-[2-(N-allyloxycarbonylamino)-ethyl]-N-p-nitrobenzyloxycarbonylpyrrolidine (890 mg, yield: 90%) was obtained from the above compound (1.03 g, 2.18 mmol) in the same manner as in REFERENCE EXAMPLE 1-5.

NMR (CDCl$_3$) δ: 1.55–2.15(4H,m). 2.34(3H,s), 2.6(1H,m), 2.9–3.5(3H,m), 3.7–4.25(2H,m), 4.57(2H,m), 5.05–5.55(5H,m), 5.32(1H,m), 7.54(2H,d,J=9 Hz), 8.26(2H,d,J=9 Hz )

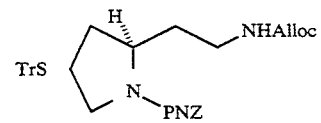
5)

To a solution of the above compound (890 mg, 2.12 mmol) in methanol (85 ml) was dropwise added 1N aqueous sodium hydroxide (2.2 ml, 2.20 mmol) under a nitrogen atmosphere, and the mixture was stirred at room temperature for 15 minutes. The mixture was acidified by an addition of 1N hydrochloric acid (2.4 ml, 2.40 mmol), and then methanol was removed in vacuo. To the residue, was added ethyl acetate (80 ml), and the mixture was washed successively with water and saturated aqueous sodium chloride, and dried over anhydrous sodium sulfate. The solvent was removed in vacuo to obtain a crude thiol.

To a solution of the crude thiol in N,N-dimethylformamide (7 ml) was added chlorotriphenylmethane (650 mg, 2.33 mmol) under a nitrogen atmosphere, and the mixture was stirred overnight at 50° C. The reaction solution was poured into water (150 ml) and extracted with ethyl acetate (50 ml×1, 20 ml×2). The organic layers were put together, then washed successively with water and saturated aqueous sodium chloride, and dried over anhydrous sodium sulfate. The solvent was removed in vacuo, and the residue was subjected to silica gel column chromatography (Wakogel ™ C-300, heptane-ethyl acetate) to give (2R,4S)-2-[2-(N-allyloxycarbonylamino)ethyl]-N-p-nitrobenzyloxycarbonyl-4-triphenylmethylthiopyrrolidine (800 mg, yield: 65%).

IR(KBr)cm$^{-1}$: 3420,1700,1610,1525,1405,1345,1250,1110,745,700
NMR (CDCl$_3$) δ:

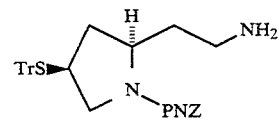
6)

1.5–2.4(4H,m), 2.5–3.45(4H,m), 3.6–5.05(2H,m), 4.55(2H,m), 4.9–5.5(4H,m), 5.5–6.0(2H,m), 7.0–7.55(17H,m), 8.25(2H,d,J=9 Hz)

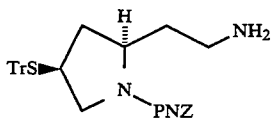
6)

To a solution of the above compound (890 mg, 1.37 mmol) in methylene chloride (14 ml) was added water (0.06 ml, 3.33 mmol) under a nitrogen atmosphere, and the mixture was evacuated, cooled with ice. Bis(triphenylphosphine)palladium(II) chloride (20 mg, 0.028 mmol) and then tributyl tin hydride (2.2 ml, 8.18 mmol) were added thereto, and the mixture was stirred at the same temperature for 10 minutes and at room temperature for 30 minutes. Further, tributyl tin hydride (2.2 ml, 8.18 mmol) was additionally added thereto under cooling with ice, and the mixture was stirred at the same temperature for 10 minutes and at room temperature for 30 minutes. The reaction solution was poured into saturated aqueous sodium hydrogencarbonate (50 ml) and extracted with methylene chloride (50 ml×3). The organic layers were put together and dried over anhydrous sodium sulfate. The solvent was removed in vacuo, and the residue was subjected to silica gel column chromatography (Wakogel ™ C-300, chloroform-methanol) to give (2R,4S)-2-(2-aminoethyl)-N-p-nitrobenzyloxycarbonyl-4-triphenylmethylthiopyrrolidine (640 mg, yield: 83%).

IR(KBr)cm$^{-1}$:
8420,3370,1695,1605,1520,1400,1345,1105,850, 740,695
NMR(CDCl$_3$) δ: 1.2–1.7(2H,m), 1.62(2H,br s), 1.8–2.4(2H,m), 2.4–3.0(4H,m), 3.32(1H,m), 3.77(1H,m), 5.11(2H,m), 7.0–7.7(17H,m), 8.26(2H,d,J=8 Hz)

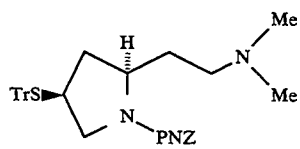
7)

To an ice-cooled solution of the above compound (350 mg, 0.624 mmol) in acetonitrile (2 ml) was added 37% formalin (0.25 ml). Sodium cyanoborohydride (80 mg, 1.27 mmol) and then acetic acid (0.035 ml, 0.611 mmol) were added thereto, and the mixture was stirred at the same temperature for 30 minutes and at room temperature overnight. Saturated aqueous sodium hydrogencarbonate (10 ml) was added to the reaction solution, and the mixture was extracted with methylene chloride (20 ml×3) The organic layers were put together and dried over anhydrous sodium sulfate. The solvent was removed in vacuo, and the residue was subjected to silica gel column chromatography (Wakogel ™ C-300, chloroform-methanol) to give the title compound (220 mg, yield: 59%).

IR(KBr)cm$^{-1}$:
3430,1700,1610,1525,1405,1345,1110,740,700
NMR(CDCl$_3$) δ: 1.15–2.4(4H,m), 2.4–3.1(4H,m), 2.51 & 2.66(total 6H, each s), 3.2–3.7(2H,m), 5.12(2H,m), 7.0–7.6(17H,m), 8.28(2H,d,J=8 Hz)

REFERENCE EXAMPLE 3

(2R,4S)-4-Acetylthio-2-[3-(N-methyl-N-p-nitrobenzyloxycarbonylamino)propyl]-N-p-nitrobenzyloxycarbonylpyrrolidine

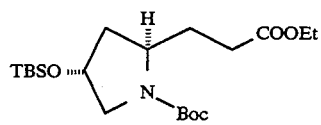
1)

To a solution of (2R,4R)-N-tert-butoxycarbonyl-4-tert-butyldimethylsiloxy-2-[(E)-2-ethoxycarbonylvinyl]-pyrrolidine (20 g, 50 mmol) in ethanol (500 ml) was added 10% palladium-carbon (5 g), and the mixture was stirred under atmospheric pressure in a hydrogen atmosphere at room temperature for 2 h. Further, 10% palladium-carbon (2 g) was added thereto, and the mixture was stirred under atmospheric pressure in a hydrogen atmosphere at room temperature for 1.5 h. The catalyst was filtered off, and the solvent was removed in vacuo. The residue was subjected to silica gel column chromatography (Wakogel ™ C-300, heptane-ethyl acetate) to give (2R,4R)-N-tert-butoxycarbonyl-4-tert-butyldimethylsiloxy-2-(2-ethoxycarbonylethyl)pyrrolidine (15.62 g, yield: 78%).

IR(KBr)cm$^{-1}$:
2930,1735,1695,1390,1365,1250,1170,1110,835, 775
NMR(CDCl$_3$) δ: 0.06(6H,s), 0.86(9H,s), 1.26(3H,t,J=7 Hz), 1.46(9H,s), 1.6–1.85(2H,m), 1.85–2.2(2H,m), 2.2–2.4(2H,m), 3.25–3.55(2H,m), 3.95(1H,m), 4.14(2H,q,J=7 Hz), 4.35(1H,m)

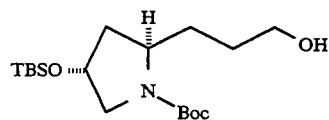
2)

To a solution of the above compound (770 mg, 1.92 mmol) in tetrahydrofuran (5 ml) were added lithium chloride (170 mg, 4.01 mmol) and then sodium borohydride (150 mg, 3.97 mmol) under a nitrogen atmosphere. Ethanol (5 ml) was added thereto, and the mixture was stirred at room temperature for 3 days. The reaction solution was acidified by an addition of 10% aqueous citric acid under cooling with ice, and then the organic solvent was distilled off. The concentrated solution was extracted with ethyl acetate (20 ml×3). The organic layers were put together, then washed successively with water and saturated aqueous sodium chloride, and dried over anhydrous sodium sulfate. The solvent was removed in vacuo, and the residue was subjected to silica gel column chromatography (Wakogel ™ C-300, hexane-ethyl acetate) to give (2R,4R)-N-tert-butoxycarbonyl-4-tert-butyldimethylsiloxy-2-(3-hydroxypropyl)-pyrrolidine (630 mg, yield: 91%).

IR(KBr)cm$^{-1}$:
3440,2930,1695,1680,1400,1365,1255,1160, 1120,1070,840,780 NMR(CDCl$_3$) δ: 0.06(6H,s), 0.87(9H,s), 1.46(9H,s), 1.35–2.05(7H,m), 3.37(2H,m), 3.68(2H,m), 3.95(1H,m), 4.35(1H,m)

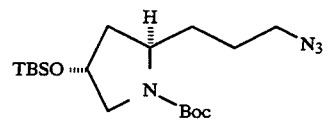
3)

To an ice-cooled solution of the above compound (580 mg, 1.61 mmol) in tetrahydrofuran (5 ml) were dropwise added triethylamine (0.45 ml, 3.23 mmol) and then methanesulfonyl chloride (0.25 ml, 3.23 mmol) under a nitrogen atmosphere, and the mixture was stirred at the same temperature for 10 minutes and at room temperature for 1 h. To the reaction solution was added ethyl acetate (100 ml), and the mixture was washed successively with 1N aqueous potassium hydrogensulfate, water, saturated aqueous sodium hydrogencarbonate, water and saturated aqueous sodium chloride, and dried over anhydrous sodium sulfate. The solvent was removed in vacuo to obtain a crude mesylate. To a solution of this crude mesylate in dimethyl sulfoxide (5 ml) was added sodium azide (350 mg, 5.38 mmol), and the mixture was stirred at 70° C. for 2 h. The reaction solution was poured into water (50 ml) and extracted with ethyl acetate (30 ml×1, 20 ml×2). The organic layers were put together, then washed successively with water and saturated aqueous sodium chloride, and dried over anhydrous sodium sulfate. The solvent was removed in vacuo, and the residue was subjected to silica gel column chromatography (Wakogel TM C-300, hexane-ethyl acetate) to give (2R,4R)-2-(3-azidopropyl)-N-tert-butoxycarbonyl-4-tert-butyldimethylsiloxypyrrolidine (500 mg, yield: 81%).

IR(KBr)cm$^{-1}$:
3450,2930,2100,1700,1395,1365,1255,1160, 1115,835,775 NMR(CDCl$_3$) δ: 0.06(6H,s), 0.86(9H,s), 1.46(9H,s), 1.35-2.05(6H,m), 3.2-3.5(4H,m), 3.90(1H,m), 4.32(1H,m)

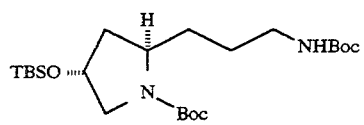

To a solution of the above compound (15.25 g, 39.65 mmol) in methanol (400 ml) was added 10% palladium-carbon (3 g), and the mixture was stirred under atmospheric pressure under a hydrogen atmosphere at room temperature for 1 h. The catalyst was filtered off, and the solvent was removed in vacuo to obtain a crude amine.

To a solution of this crude amine in dioxane (100 ml) was added S-tert-butoxycarbonyl-4,6-dimethyl-2-mercaptopyrimidine (10 g, 41.61 mmol), and the mixture was stirred at room temperature for 3 days. To the reaction solution was added ethyl acetate (600 ml), and the mixture was washed successively with 1N aqueous potassium hydrogensulfate, water and saturated aqueous sodium chloride, and then dried over anhydrous sodium sulfate. The solvent was removed in vacuo, and the residue was subjected to silica gel column chromatography (Wakogel TM C-300, heptane-ethyl acetate) to give (2R,4R)-N-tert-butoxycarbonyl-2-[3-(tertbutoxycarbonylamino)propyl]-4-tert-butyldimethylsiloxypyrrolidine (16.19 g, yield: 89%).

IR(KBr)cm$^{-1}$:
3350,2930,1695,1520,1455,1390,1365,1250, 1170,840,775, NMR (CDCl$_3$) δ: 0.06(6H,s), 0.86(9H,s), 1.2-1.4(2H,m), 1.43(9H,s), 1.45(9H,s), 1.6-2.1(4H,m), 3.13(2H,m), 3.25-3.5(2H,m), 3.89(1H,m), 4.32(1H,m), 4.5-4.8 (1H,br)

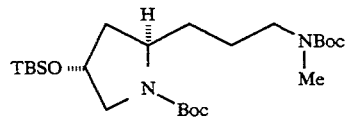

(2R,4R)-N-tert-Butoxycarbonyl-2-[3-(N-tert-butoxycarbonyl-N-methylamino)propyl]-4-tert-butyldimethylsiloxypyrrolidine (15.49 g, yield: 93%) was obtained from the above compound (16.19 g, 35.29 mmol) in the same manner as in REFERENCE EXAMPLE 1-2.

IR(KBr)cm$^{-1}$:
2930,1695,1395,1365,1255,1165,835,775 NMR(CDCl$_3$) δ: 0.06(6H,s), 0.87(9H,s), 1.2-1.4(2H,m), 1.45(18H,s), 1.6-2.1(4H,m), 2.85(3H,s), 3.1-3.5(4H,m), 3.90(1H,m) , 4.32(1H,m)

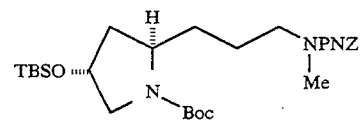

(2R,4R)-4-Hydroxy-2-[3-(N-methyl-N-p-nitrobenzyloxycarbonylamino)propyl]-N-pitrobenzyloxycarbonylpyrrolidine (15.65 g, yield: 92%) was obtained from the above compound (15.49 g, 32.77 mmol) in the same manner as in REFERENCE EXAMPLE 1-3.

IR(KBr)cm$^{-1}$:
3390,1700,1670,1600,1515,1435,1405,1340, 1210,1150,850,735 NMR (CDCl$_3$) δ: 1.25-2.2(7H,m), 2.92(3H,s), 3.31(2H,m), 3.48(1H,m), 3.63(1H,m), 4.05(1H,m), 4.45(1H,m), 5.21(4H,s), 7.51(4H,d,J=8 Hz), 8.21(4H,d,J=8 Hz)

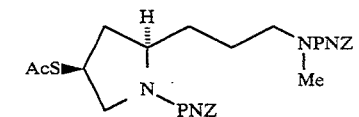

The title compound (14.30 g, yield: 82%) was obtained from the above compound (15.65 g, 30.30 mmol) in the same manner as in REFERENCE EXAMPLES 1-4 and 1-5.

IR(KBr)cm$^{-1}$:
2940,1700,1605,1520,1400,1345,1200,1105,855, 765,735,625 NMR(CDCl$_3$) δ: 1.3-2.15(6H,m), 2.34(3H,s), 2.52(1H,m), 2.93(3H,s), 3.18(1H,m), 3.31(2H,m), 3.88(1H,m), 4.12(1H,m), 5.21(4H,s), 7.51(4H,d,J=9 Hz), 8.22(4H,d,J=9 Hz)

REFERENCE EXAMPLE 4

(1R,5S,6S)-2-[(2S,4S)-2-(Acetylaminomethyl)pyrrolidin-4-ylthio]-6-[(R)-1-hydroxyethyl]-1-methyl-1-carbapen-2-em-3-carboxylic Acid

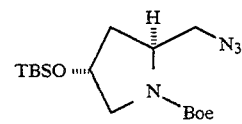

To an ice-cooled solution of (2S,4R)-N-tert-butoxycarbonyl-4-tert-butyldimethylsiloxy-2-hydroxymethylpyrrolidine (1.66 g, 5 mmol) in tetrahydrofuran (10 ml) was added triethylamine (1.4 ml, 10 mmol) and then dropwise added methanesulfonyl chloride (0.76 ml, 9.82 mmol) under a nitrogen atmosphere, and the mixture was stirred at the same temperature for 30 minutes. The reaction solution was poured into ice water (100 ml) and extracted with ethyl acetate (50 ml×3). The organic layers were put together, then washed successively with 1N aqueous potassium hydrogensulfate, water, saturated aqueous sodium hydrogencarbonate, water and saturated sodium chloride, and dried over anhydrous sodium sulfate. The solvent was removed in vacuo to obtain a crude mesylate.

To a solution of this mesylate in dimethyl sulfoxide (15 ml) was added sodium azide (1.10 g, 15.94 mmol), and the mixture was stirred under a nitrogen atmosphere at 70° C. for 2 h. The reaction solution was poured into water (100 ml) and extracted with ethyl acetate (50 ml×3). The organic layers were put together, then washed successively with water and saturated aqueous sodium chloride, and dried over anhydrous sodium sulfate. The solvent was removed in vacuo, and the residue was subjected to silica gel column chromatography (Wakogel TM C-300, heptane-ethyl acetate) to give (2S,4R)-2-azidomethyl-N-tert-butoxycarbonyl-4-tert-butyldimethylsiloxypyrrolidine (1.19 g, yield: 67%).

IR(KBr)cm$^{-1}$:
2940,2110,1700,1395,1365,1255,1165,1120,840, 775
NMR (CDCl$_3$) δ: 0.07(6H,s), 0.86(9H,s), 1.47(9H,s), 1.96(2H,m), 3.2–3.6(4H,m), 4.10(1H,m), 4.38(1H,m)

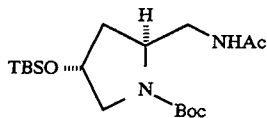
2)

To a solution of the above compound (1.19 g, 3.34 mmol) in methanol (33 ml) was added 10% palladium-carbon (240 mg), and the mixture was stirred under atmospheric pressure under a hydrogen atmosphere at room temperature for 1 h. The catalyst was filtered off, and the solvent was removed in vacuo to obtain a crude amine.

To an ice-cooled solution of this crude amine in methylene chloride (10 ml) was added triethylamine (0.94 ml, 6.74 mmol) and then dropwise added acetic anhydride (0.64 ml, 6.78 mmol) under a nitrogen atmosphere, and the mixture was stirred at the same temperature for 1 h. The reaction solution was poured into water (100 ml) and extracted with ethyl acetate (100 ml×1, 30 ml×2). The organic layers were put together, and the mixture was washed successively with 1N aqueous potassium hydrogensulfate, water, saturated aqueous sodium hydrogencarbonate, water and saturated aqueous sodium chloride, and then dried over anhydrous sodium sulfate. The solvent was removed in vacuo, and the residue was subjected to silica gel column chromatography (Wakogel TM C-300, heptane-ethyl acetate) to give (2S,4R)-2-acetylaminomethyl-N-tert-butoxycarbonyl-4-tert-butyldimethylsiloxypyrrolidine (1.18 g, yield: 95%).

IR(KBr)cm$^{-1}$:
2920,1695,1655,1550,1395,1360,1250,1160, 1115,835,770
NMR (CDCl$_3$) δ: 0.05(6H,S), 0.86(9H,s), 1.47(9H,s), 1.6–1.9(2H,m), 1.98(3H,S), 3.12(1H,m), 3.25–3.55(3H,m), 4.11(1H,m), 4.33(1H,m), 7.52(1H,br s)

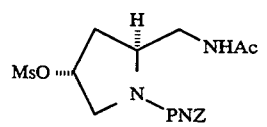
3)

The above compound (1.15 g, 3.09 mmol) was dissolved in trifluoroacetic acid (10 ml), and the solution was stirred overnight at room temperature. Trifluoroacetic acid was removed in vacuo, and the residue was distilled a few times after an addition of benzene to obtain a crude amino alcohol.

To a solution of this crude amino alcohol in a mixture of dioxane (7.5 ml)-water (2.5 ml) were sequentially added sodium hydrogencarbonate (2.6 g, 30.9 mmol) and the 4,6-dimethyl-2-(p-nitrobenzyloxycarbonylthio)-pyrimidine (990 mg, 3.10 mmol), and the mixture was stirred at room temperature for 3 h. To the reaction solution was added ethyl acetate (150 ml), and the mixture was washed successively with water, 1N aqueous potassium hydrogensulfate, water, saturated aqueous sodium hydrogencarbonate, water and saturated aqueous sodium chloride, and dried over anhydrous sodium sulfate. The solvent was removed in vacuo to obtain a crude alcohol. To an ice-cooled solution of this crude alcohol in tetrahydrofuran (10 ml) were dropwise added triethylamine (0.86 ml, 6.17 mmol) and then methanesulfonyl chloride (0.48 ml, 6.20 mmol) under a nitrogen atmosphere, and the mixture was stirred at the same temperature for 30 minutes. To the reaction solution was added ethyl acetate (150 ml), and the mixture was washed successively with water, 1N aqueous potassium hydrogensulfate, water, saturated sodium hydrogencarbonate, water and saturated aqueous sodium chloride, and dried over anhydrous sodium sulfate. The solvent was removed in vacuo, and the residue was subjected to silica gel column chromatography (Wakogel TM C-300, chloroform-methanol) to give (2R,4R)-2-acetylaminomethyl-4-methanesulfonyloxy-N-P-nitrobenzyloxycarbonylpyrrolidine (740 mg, yield: 58%).

IR(KBr)cm$^{-1}$:
3400,1700,1660,1520,1430,1400,1340,1170, 1110,955,900
NMR(CDCl$_3$) δ: 1.80(1H,s), 1.95–2.2(1H,m), 1.98(3H,s), 2.47(1H,dd,J=8,14 Hz), 3.05(3H,s), 3.2–3.45(1H,m), 3.45–3.8 (2H,m ), 4.0–4.25(2H,m), 5.15–5.35(2H,m), 6.82(1H,br s) , 7.54(2H,d,J=9 Hz) , 8.25(2H,d,J=9 Hz)

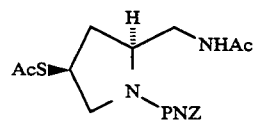
4)

To a solution of the above compound (690 mg, 1.66 mmol) in N,N-dimethylformamide (7 ml) were added potassium thioacetate (380 mg, 3.33 mmol) and sodium iodide (370 mg, 2.47 mmol). The mixture was stirred under a nitrogen atmosphere at 70° C. for 3 h. The reaction solution was poured into ice water (150 ml) and extracted with ethyl acetate (100 ml×1, 50 ml×2). The organic layers were put together, and the mixture was washed successively with 10% aqueous sodium sulfite and saturated aqueous sodium chloride, and dried over anhydrous sodium sulfate. The solvent was removed in vacuo, and the residue was subjected to silica gel column chromatography (Wakogel TM C-300, heptane-ethyl acetate) to give (2S,4S)-2-acetylaminomethyl-4-acetylthio-N-p-nitrobenzyloxycarbonylpyrrolidine (560 mg, yield: 85%).

IR(KBr)cm$^-$:
3330,1700,1680,1640,1520,1425,1345,1200, 1125,1105,630 NMR (CDCl$_3$) δ: 1.55–1.9 (1H,m), 1.96(3H,s), 2.34(3H,s), 2.58(1H,m), 3.1–3.45 (2H,m), 3.63 (1H,m), 3.88(1H,m), 3.95–4.25 (2H,m), 5.25(2H,s), 6.99(1H,br s), 7,54(2H,d,J=9 Hz), 8.25(2H,d,J=9 Hz)

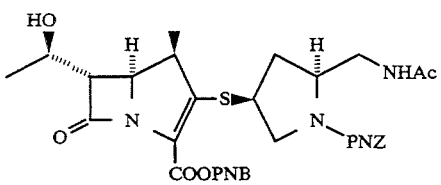
5)

p-Nitrobenzyl (1R,5S,6S)-2-[(2S,4S)-2-acetylaminomethyl-N-p-nitrobenzyloxycarbonylpyrrolidin-4-ylthio]6-[(R)-1-hydroxyethyl]-1-methyl-1-carbapen-2-em-3-carboxylate (420 mg, yield: 88%) was obtained from the above compound (270 mg, 0.683 mmol) and p-nitrobenzyl (1R,5S,6S)-2-diphenoxyphosphoryloxy-6-[(R)-1-hydroxyethyl]-1-methyl-1-carbapen-2-em-3-carboxylate (430 mg, 0.723 mmol) in the same manner as in EXAMPLE 1-1.

IR(KBr)cm$^{-1}$: 3400,1770,1700,1660,1520,1345,1200,1105

NMR(CDCl$_3$) δ: 1.28(3H,d,J=7 Hz), 1.36(3H,d,J=6 Hz), 1.6–2.15(2H,m), 1.96(3H,s), 2.59(1H,m), 3.2–3.45(4H,m), 3.45–3.85(2H,m), 3.9–4.2 (2H,m), 4.2–4.3 (2H,m), 5.1–5.55(4H,m), 6.87(1H,br s), 7.45–7.75(4H,m), 8.15–8.3(4H,m)

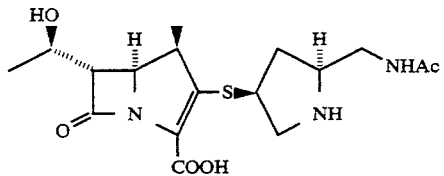
6)

The title compound (130 mg, yield: 64%) was obtained from the above compound (370 mg, 0.530 mmol) in the same manner as in EXAMPLE 1-2.

IR(KBr)cm$^{-1}$: 3400,1755,1660,1600,1550,1390,1285
NMR(D$_2$O) δ: 1.14(3H,d,J=7 Hz), 1.21(3H,d,J=6 Hz), 1.66(1H,m), 1.96(3H,m), 2.65(1H,m), 3.1–3.45(3H,m), 3.45–3.7(3H,m), 3.7–4.05(2H,m), 4.05–4.3(2H,m) UVλ$_{max}$ (0.1M 3-morpholinopropane sulfonate buffer, pH 7.0): 298 nm (ε=8800)

We claim:
1. A compound of the formula:

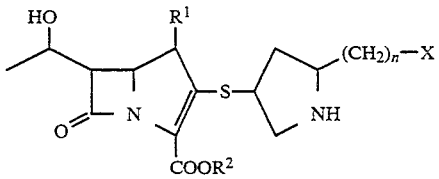
(I)

wherein $R^1$ is a hydrogen atom or a methyl group, $R^2$ is a hydrogen atom or a negative charge, X is a group of —N($R^3$)$R^4$ (wherein $R^3$ is a lower alkyl group, and $R^4$ is a hydrogen atom or a lower alkyl group) or a group of —N$^+$($R^5$)($R^6$)$R^7$ (wherein each of $R^5$, $R^6$ and $R^7$ which may be the same or different, is a lower alkyl group), and n is an integer of from 2 to 4; or a pharmaceutically acceptable salt or ester thereof.

2. The compound according to claim 1, which has a steric configuration of (5R,6S,8R) or (1R,5S,6S,8R).

3. The compound according to claim 1, wherein $R^1$ is a methyl group.

4. The compound according to claim 1, which is
   (5R,6S)-6-[(R)-1-hydroxyethyl]-2-[(2R,4S)-2-[2-(methylamino)ethyl]pyrrolidin-4-ylthio]-1-carbapen-2-em-3-carboxylic acid,
   (1R,5S,6S)-6-[(R)-1-hydroxyethyl]-1-methyl-2-[(2R,4S)-2-[2-(methylamino)ethyl]pyrrolidin-4-ylthio]-1-carbapen-2-em-3-carboxylic acid,
   (5R,6S)-2-[(2R,4S)-2-[2-(dimethylamino)ethyl]pyrrolidin-4-ylthio]-6-[(R)-1-hydroxyethyl]-1-carbapen-2-em-3-carboxylic acid,
   (1R,5S,6S)-2-[(2R,4S)-2-[2-(dimethylamino)ethyl]-pyrrolidin-4-ylthio]-6-[(R)-1-hydroxyethyl]-1-methyl-1-carbapen-2-em-3-carboxylic acid,
   (5R,6S)-6-[(R)-1-hydroxyethyl]-2-[(2R,4S)-2-[3-(methylamino)propyl]pyrrolidin-4-ylthio]-1-carbapen-2-em-3-carboxylic acid or
   (1R,5S,6S)-6-[(R)-1-hydroxyethyl]-1-methyl-2-[(2R,4S)-2[3-(methylamino)propyl]pyrrolidin-4-ylthio]-1-carbapen-2-em-3-carboxylic acid.

5. An antibacterial agent comprising an antibacterially effective amount of the compound of the formula (I) as defined in claim 1 or a pharmaceutically acceptable salt or ester thereof, and a pharmaceutically acceptable carrier or diluent.

* * * * *